(12) United States Patent
Kishishita et al.

(10) Patent No.: US 10,357,581 B2
(45) Date of Patent: Jul. 23, 2019

(54) STERILIZER AND STERILIZING METHOD

(71) Applicant: YUYAMA MFG. CO., LTD., Toyonaka-shi, Osaka (JP)

(72) Inventors: Yoshitaka Kishishita, Toyonaka (JP); Hajime Mishima, Toyonaka (JP)

(73) Assignee: YUYAMA MFG. CO., LTD., Toyonaka-shi, Osaka (JP)

( * ) Notice: Subject to any disclaimer, the term of this patent is extended or adjusted under 35 U.S.C. 154(b) by 0 days.

(21) Appl. No.: 15/322,022

(22) PCT Filed: Jun. 24, 2015

(86) PCT No.: PCT/JP2015/068124
§ 371 (c)(1),
(2) Date: Mar. 31, 2017

(87) PCT Pub. No.: WO2015/199108
PCT Pub. Date: Dec. 30, 2015

(65) Prior Publication Data
US 2017/0202987 A1    Jul. 20, 2017

(30) Foreign Application Priority Data

Jun. 24, 2014 (JP) .................................. 2014-129665
Oct. 16, 2014 (JP) .................................. 2014-211973

(51) Int. Cl.
*A61L 2/07* (2006.01)
(52) U.S. Cl.
CPC ...................................... *A61L 2/07* (2013.01)
(58) Field of Classification Search
CPC ............................................................ A61L 2/07
See application file for complete search history.

(56) References Cited

U.S. PATENT DOCUMENTS 5,906,800 A * 5/1999 Napierkowski ........... A61L 2/07
122/40

FOREIGN PATENT DOCUMENTS

| JP | H09-72493 A | 3/1997 |
| JP | H09-327503 A | 12/1997 |
| JP | H10-234832 A | 9/1998 |
| JP | H11-56975 A | 3/1999 |
| JP | H11-267184 A | 10/1999 |

(Continued)

OTHER PUBLICATIONS

ISA/JP, International Search Report issued in PCT/JP2015/068124, dated Oct. 6, 2015, total 3 pages with English translation.

(Continued)

*Primary Examiner* — Kevin Joyner
(74) *Attorney, Agent, or Firm* — Masuvalley & Partners

(57) ABSTRACT

Systems and methods are provided to reduce noise generated by water and gas discharged after a sterilization treatment, and to prevent adhesion of condensation water on an object to be sterilized. The sterilizer according to the embodiments of the present invention may include a can body having a heater and capable of housing an object to be sterilized; a steam discharge pipe connected to the can body and having an opening and closing means for opening and closing a channel to enable discharging of steam; and a discharged steam tank provided partway along the steam discharge pipe and having a greater channel cross-sectional area than that of the steam discharge pipe.

12 Claims, 11 Drawing Sheets

(56) References Cited

FOREIGN PATENT DOCUMENTS

| | | |
|---|---|---|
| JP | 2001-170140 A | 6/2001 |
| JP | 2011-170142 A | 6/2001 |
| JP | 2009-291456 A | 12/2009 |
| JP | 2012-040185 A | 3/2012 |
| WO | 02/45758 A1 | 6/2002 |
| WO | 2013/114539 A1 | 8/2013 |

OTHER PUBLICATIONS

EPO, Extended European Search Report dated Feb. 1, 2018 in EP Patent Application No. 15812414.9, total 9 pages.

* cited by examiner

Fig. 5

| Processing Details | | Preparation Treatment | | | | | Heating Treatment | | | Sterilization Treatment | | |
|---|---|---|---|---|---|---|---|---|---|---|---|---|
| Control target | Trigger | Start Button | Close Door | 30 sec passed | At Preheat Temp. | At Prescribed Water Level | 95°C | Condition Satisfied | At Sterilization Temperature | Equilibrium Time Passed | Sterilization Time Passed |
| Door Motor | OPEN / CLOSE / OFF | | | | | | | | | | |
| Sterilization Heater | ON / OFF | | | | | | | | | | |
| Drying Heater | ON / OFF | | | | | | | | | | |
| Steam Discharge Solenoid Valve SV1 | OPEN / CLOSE | | | | | | | | | | |
| Exhaust Gas Solenoid Valve SV2 | OPEN / CLOSE | | | | | | | | | | |
| Water Supply Solenoid Valve SV3 | OPEN / CLOSE | | | | | | | | | | |
| Water Discharge Solenoid Valve SV4 | OPEN / CLOSE | | | | | | | | | | |
| Air Solenoid Valve SV5 | OPEN / CLOSE | | | | | | | | | | |
| Air Pump AP | OPEN / CLOSE | | | | | | | | | | |

Fig. 6

| Processing Details | | Steam and Water Discharge Treatment | | | | Drying Treatment | | |
|---|---|---|---|---|---|---|---|---|
| Control target | Trigger | 80 sec passed | 10sec passed | 10 sec passed | 80 sec passed | 30 sec passed | Drying Time passed | Stop Button |
| Door Motor | OPEN / CLOSE / OFF | | | | | | | |
| Sterilization Heater | ON / OFF | | | | | | | |
| Drying Heater | ON / OFF | | | | | | | |
| Steam Discharge Solenoid Valve SV1 | OPEN / CLOSE | | | | | | | |
| Exhaust Gas Solenoid Valve SV2 | OPEN / CLOSE | | | | | | | |
| Water Supply Solenoid Valve SV3 | OPEN / CLOSE | | | | | | | |
| Water Discharge Solenoid Valve SV4 | OPEN / CLOSE | | | | | | | |
| Air Solenoid Valve SV5 | OPEN / CLOSE | | | | | | | |
| Air Pump AP | OPEN / CLOSE | | | | | | | |

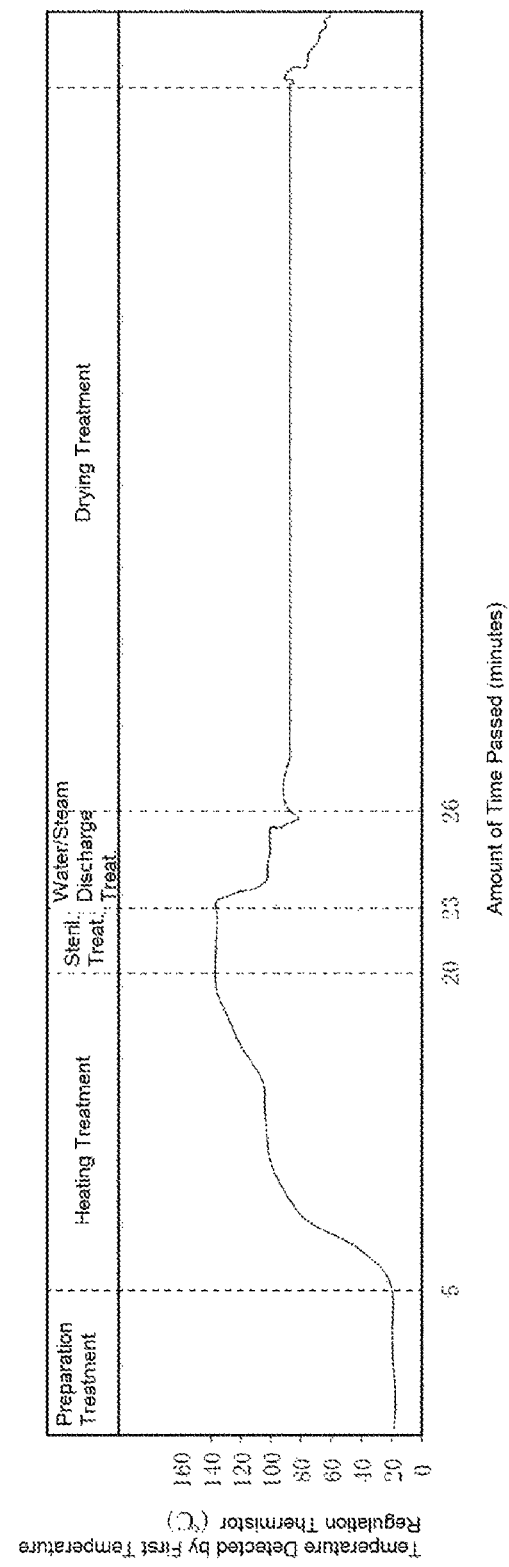

Fig. 13

| Processing Details | | Steam and Water Discharge Treatment | | | | |
|---|---|---|---|---|---|---|
| Trigger / Control Target | | 60 sec passed | 20 sec passed | 30 sec passed | 70 sec passed | 90 sec passed |
| Door Motor | OPEN CLOSE OFF | | | | | |
| Sterilization Heater | ON OFF | | | | | |
| Drying Heater | ON OFF | | | | | |
| Steam Discharge Solenoid Valve SV1 | OPEN CLOSE | | | | | |
| Exhaust Gas Solenoid Valve SV2 | OPEN CLOSE | | | | | |
| Water Supply Solenoid Valve SV3 | OPEN CLOSE | | | | | |
| Water Discharge Solenoid Valve SV4 | OPEN CLOSE | | | | | |
| Air Solenoid Valve SV5 | OPEN CLOSE | | | | | |
| Air Pump AP | OPEN CLOSE | | | | | |

STERILIZER AND STERILIZING METHOD

RELATED APPLICATIONS

This application is a national phase application under 35 U.S.C. § 371 of International Patent Application No. PCT/JP2015/068124 filed on Jun. 24, 2015, which claims priority under 35 U.S.C. § 119 to Japanese Patent Application No. 2014-129665 filed on Jun. 24, 2014, and Japanese Patent Application No. 2014-211973 filed on Oct. 16, 2014, which are hereby expressly incorporated by reference in their entirety for all purposes.

TECHNICAL FIELD

The present invention relates to a sterilizer and a sterilizing method.

BACKGROUND ART

Conventionally, a sterilizer which uses internal steam pressure to discharge water after completing a sterilization treatment, and releases the steam pressure after the discharge of water has been completed is known (for example, see patent document 1: Japanese Unexamined Patent Application Publication No. H09-327503).

However, in the abovementioned conventional sterilizer, no consideration is given whatsoever to the noise that is generated when discharging residual water and steam from the inside.

An object of the present invention is to reduce the noise that is generated by discharged water and exhaust gas after a sterilization treatment.

SUMMARY OF THE INVENTION

As means for solving the abovementioned problem, the present invention provides a sterilizer including a can body having a heater, and capable of housing an object to be sterilized; a steam discharge pipe connected to the can body and having an opening and closing means for opening and closing a channel to enable discharging of steam; and a discharged steam tank provided partway along the steam discharge pipe, and having a greater channel cross-sectional area than a channel cross-sectional area of the steam discharge pipe.

Moreover, as means for solving the abovementioned problem, the present invention provides a sterilizer including a can body capable of housing an object to be sterilized; a steam generator for generating steam and supplying the steam to the can body; a steam discharge pipe connected to the can body, and having an opening and closing means for opening and closing a channel to enable discharging of steam; and a discharged steam tank provided partway along the steam discharge pipe, and having a greater channel cross-sectional area than a channel cross-sectional area of the steam discharge pipe.

Through these configurations, steam discharged from the can body to the steam discharge pipe temporarily flows into the discharged steam tank, and the flow rate decreases. Moreover, the channel cross-sectional area is increased inside the discharged steam tank, and therefore the sound (direct sound) that is generated when the steam flows into the discharged steam tank, and the reflected sound on the inside wall of the discharged steam tank mutually cancel out each other. Furthermore, steam discharged from the discharged steam tank is subjected to flow resistance, and therefore the flow rate is further reduced. As a result, the noise that is generated when the steam flows out from the steam discharge pipe can be significantly suppressed.

It is preferred that the steam discharge pipe is made from an upstream side piping, which is a path from the can body to the discharged steam tank, and a downstream side piping connected to the discharged steam tank and a discharged steam cooling unit for cooling the steam discharged from the discharged steam tank before the steam reaches outside, and a channel cross-sectional area of the downstream side piping is smaller than a channel cross-sectional area of the upstream side piping.

Through this configuration, the flow rate at the downstream side piping is further reduced, and the generation of noise can be further suppressed.

It is preferred that a second steam discharge pipe connected to the discharged steam tank and the discharged steam cooling unit, and having an opening and closing means for opening and closing a channel is connected.

Through this configuration, in addition to the steam discharge pipe, the second steam discharge pipe can also be communicated with the discharged steam tank, and therefore the time required to discharge steam can be reduced.

It is preferred that a second steam discharge pipe connected to the discharged steam tank and the discharged steam cooling unit, and having an opening and closing means for opening and closing a channel is connected, and the second steam discharge pipe has a larger channel cross-sectional area than that of the downstream side piping of the steam discharge pipe.

Through this configuration, the time required to discharge steam can be further reduced.

It is preferred that the discharged steam cooling unit is a water storage tank.

Through this configuration, a special configuration for cooling the discharged steam is not required, and a problem of burning surrounding people by being exposed to the discharged steam or the like does not occur.

It is preferred that a piping connected to the can body and having an opening and closing means for opening and closing a channel to enable discharging of water is provided, and the piping is branched into a water supply pipe capable of supplying the water from the water storage tank and a drainage pipe capable of discharging the water to the water storage tank.

Through this configuration, a portion of the piping is used in common for both water supply and water discharge, and the branch portion can be formed into a structure suited for both water supply and water discharge.

Axial center positions of the upstream side piping and the downstream side piping connected to the discharged steam tank may also be displaced.

Through this configuration, the direct sound of noise, which is generated when the steam from the can body is discharged from the upstream side piping to the discharged steam tank, is not transmitted outside through the downstream side piping, and therefore more excellent sound insulation can be exhibited.

Moreover, as means for solving the abovementioned problem, the present invention provides a sterilizer including a can body having a heater, and capable of housing an object to be sterilized; a steam discharge pipe connected to the can body and opening and closing a channel to enable discharging of steam; and a discharged steam tank provided so as to be branched from the steam discharge pipe, and having a greater channel cross-sectional area than a channel cross-sectional area of the steam discharge pipe, wherein the steam discharge pipe has respective first and second opening and closing means at upstream and downstream sides through a branching position.

Furthermore, as means for solving the abovementioned problem, the present invention provides a sterilizer including a can body capable of housing an object to be sterilized; a steam generator for generating steam and supplying the steam to the can body; a steam discharge pipe connected to the can body and opening and closing a channel to enable discharging of steam; and a discharged steam tank provided so as to be branched from the steam discharge pipe, and having a greater channel cross-sectional area than a channel cross-sectional area of the steam discharge pipe, wherein the steam discharge pipe has respective opening and closing means at upstream and downstream sides through a branching position.

Through these configuration, if steam is discharged (discharged steam) from the can body, the first opening and closing means is opened, and the second opening and closing means is closed to allow the steam to first flow into the discharged steam tank. Accordingly, the leakage externally of noise generated at this time can be prevented. Steam pressure in the discharged steam tank is not very high, and therefore the steam can be discharged externally without the generation of noise by closing the first opening and closing means and opening the second opening and closing means.

Moreover, as means for solving the abovementioned problem, the present invention provides a sterilizer including a can body having a heater, and capable of housing an object to be sterilized; and a steam discharge pipe connected to the can body and having an opening and closing means for opening and closing a channel, wherein the steam discharge pipe has an expanded diameter part at which an inner diameter dimension of the steam discharge pipe is enlarged.

Moreover, as means for solving the abovementioned problem, the present invention provides a sterilizer including a can body capable of housing an object to be sterilized; a steam generator for generating steam and supplying the steam to the can body; and a steam discharge pipe connected to the can body and having an opening and closing means for opening and closing a channel, wherein the steam discharge pipe has an expanded diameter part at which an inner diameter dimension of the steam discharge pipe is enlarged.

Through these configurations, the flow rate of the steam discharged to the steam discharge pipe is reduced at the expanded diameter part, and then further reduced due to flow resistance caused by once again reducing the inner diameter dimension. Accordingly, the generation of noise when steam flows out from the steam discharge pipe can be suppressed.

Moreover, as means for solving the abovementioned problem, the present invention provides a sterilizing method using a sterilizer including a can body capable of housing an object to be sterilized, a steam discharge pipe connected to the can body and having an opening and closing means for opening and closing a channel to enable discharging of steam, and a discharged steam tank provided partway along the steam discharge pipe, and having a greater channel cross-sectional area than a channel cross-sectional area of the steam discharge pipe, wherein the sterilizing method includes performing a sterilization treatment in which the object to be sterilized is sterilized inside the can body; and performing a steam discharge process after the completion of the sterilization treatment, the steam discharge process in which the steam is discharged from the can body by opening a channel of the channel of the steam discharge pipe using the opening and closing means.

Moreover, as means for solving the abovementioned problem, the present invention provides a sterilizing method using a sterilizer including a can body capable of housing an object to be sterilized, a steam discharge pipe connected to the can body, and having an opening and closing means for opening and closing a channel to enable discharging of steam, a piping connected to the can body and having an opening and closing means for opening and closing a channel to enable discharging of water, and a discharged steam tank provided partway along the steam discharge pipe, and having a greater channel cross-sectional area than a channel cross-sectional area of the steam discharge pipe, wherein the sterilizing method includes performing a sterilization treatment in which the object to be sterilized is sterilized inside the can body; and performing a steam discharge process after the completion of the sterilization treatment, the steam discharge process in which the steam is discharged from the can body by opening the channel of the steam discharge pipe, and performing a water discharge process in which the water is discharged from the can body by opening the channel of the piping with a first opening and closing means while continuing the discharging of steam.

A second water discharge process, in which the discharging of steam is stopped by closing the steam discharge pipe, and the water is discharged from the can body while maintaining an opened state of the piping, may be further performed.

Furthermore, as means for solving the abovementioned problem, the present invention provides a sterilizing method using a sterilizer including a can body capable of housing an object to be sterilized, a steam discharge pipe connected to the can body and having an opening and closing means for opening and closing a channel to enable discharging of steam, a piping connected to the can body and having an opening and closing means for opening and closing a channel to enable discharging of water, a discharged steam tank provided partway along the steam discharge pipe, and having a greater channel cross-sectional area than a channel cross-sectional area of the steam discharge pipe, and a second steam discharge pipe connected to the steam discharge pipe, and having a second opening and closing means for opening and closing a channel to enable the discharging of steam. It is preferred that the sterilizing method includes performing a sterilization treatment in which the object to be sterilized is sterilized inside the can body; and performing a steam discharge process after the completion of the sterilization process, the steam discharge process in which the channel of the steam discharge pipe is opened for a prescribed time, and then the second opening and closing means provided in the second steam discharge pipe connected to the steam discharge pipe is opened.

It is preferred that the opening and closing means of the channel of the piping connected to the can body opens and closes at a prescribed cycle during the water discharge process.

Furthermore, as means for solving the abovementioned problem, the present invention provides a sterilizing method using a sterilizer including a can body capable of housing an object to be sterilized, a steam discharge pipe connected to the can body and having an opening and closing means for opening and closing a channel to enable discharging of steam, and a discharged steam tank provided partway along the steam discharge pipe, and having a greater channel cross-sectional area than a channel cross-sectional area of the steam discharge pipe, wherein the steam discharge pipe includes an upstream side piping forming a path from the can body to the discharged steam tank, and a downstream side piping connected to the discharged steam tank and a discharged steam cooling unit for cooling the steam discharged from the discharged steam tank before the steam reaches outside, wherein a channel cross-sectional area of the downstream side piping is smaller than a channel cross-sectional area of the upstream side piping, and wherein a second steam discharge pipe connected to the discharged steam tank and the discharged steam cooling unit, and having an opening and closing means for opening and closing a channel is connected. The sterilizing method includes performing a sterilization treatment in which the object to be sterilized is sterilized inside the can body; performing a steam discharge process after the completion of the sterilization treatment, the steam discharge process in which the steam is discharged from the can body by opening the channel of the steam discharge pipe; performing a first water discharge process in which water is discharged from the can body by opening a channel of a piping while maintaining an opened state of the steam discharge pipe; performing a second water discharge process after the completion of the first water discharge process, the second water discharge process in which the discharging of steam is stopped by closing the steam discharge pipe, and the water is discharged from the can body while maintaining the opened state of the piping; and performing a gas discharge process in which steam is discharged from the can body by opening the channel of the steam discharge pipe and opening the channel of the second steam discharge pipe.

According to the present invention, a discharged steam tank is provided partway along the steam discharge pipe which guides steam discharged from the can body, and therefore the generation of noise can be suppressed. This makes it possible to provide a configuration suited for installation in a quiet location such as a hospital.

BRIEF DESCRIPTION OF THE DRAWINGS

FIG. 5 is a timing chart showing the operations of the sterilizer of FIG. 1.

FIG. 6 is a timing chart showing the operations of the sterilizer of FIG. 1.

FIG. 7 is a graph showing the change in temperature detected by a first temperature regulation thermistor of FIG. 4.

FIG. 13 is a timing chart showing, of the operations of the sterilizer according to the other embodiment, the operation of steam and water discharge processing.

DETAILED DESCRIPTION OF THE INVENTION

An embodiment according to the present invention is described below in accordance with the attached drawings. Note that in the following description, as necessary, terminology indicating a specific direction or position (for example, terms including "up", "down", "side" and "end") are used, but such terms are used for the purpose of facilitating the understanding of the invention with reference to the drawings, and the technical scope of the present invention is not limited by the meaning of such terms. Moreover, the following description is essentially merely an illustration by example, and is not intended to limit the present invention, its applicable products, or applications thereof. Furthermore, the drawings are schematic figures, and the ratios and the like of each of the dimensions may vary from the actual invention.

Figure 1:
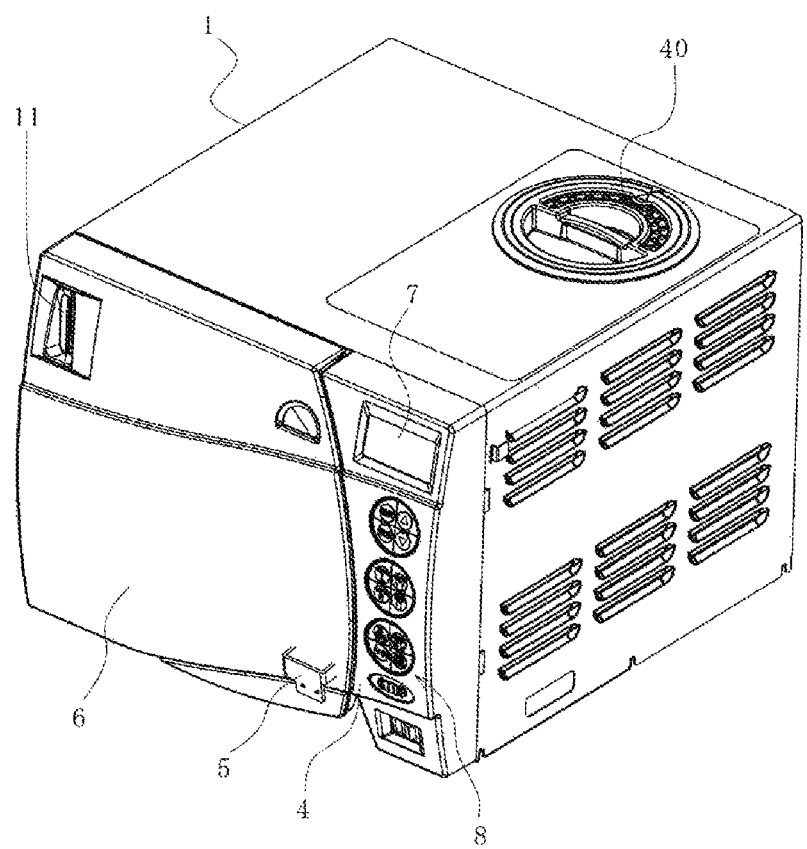
FIG. 1 is a perspective view showing the external appearance of a sterilizer according to the present embodiment.
Figure 2:
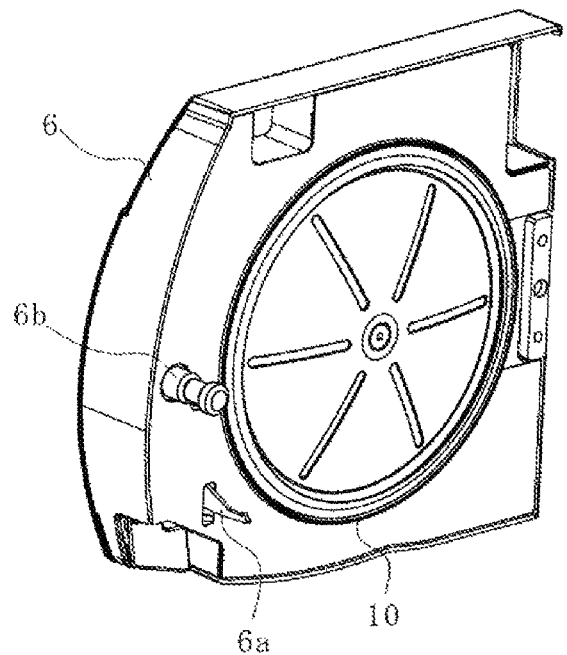
FIG. 2 is a perspective view showing a state viewed from the inside of only a door separated from the sterilizer shown in FIG. 1.

FIG. 1 shows a sterilizer according to the present embodiment. In such a sterilizer, as shown in FIG. 2, an object to be sterilized 3 is housed in a can body 2 accommodated in a device body 1. Supplied water is heated by a sterilization heater 12 provided at a base part inside the can body 2 to produce steam, and the object to be sterilized 3 is sterilized.

As shown in FIG. 1, the front surface of the device body 1 is configured with a display operation panel 4 at the right side part as viewed from the front, and a door 6 provided with a handle 5 is provided at the left side thereof.

The display operation panel 4 is provided, in order from the top side, with a liquid crystal panel 7, various operation buttons 8, and a power switch 9. From the top side, the operation buttons 8 are configured from setting buttons for implementing various settings, temperature selection buttons for selecting the sterilization temperature, and treatment selection buttons for selecting the treatment details.

The door 6 is rotatably attached to the device body 1 around a support shaft (not illustrated) at the left end as viewed from the front. As shown in FIG. 2, an engaging piece 6a and a lock pin 6b project from the inner surface (device body side surface) of the door 6. The engaging piece 6a is provided so as to be capable of swinging, and when the door 6 is in a closed state with respect to the device body 1, the engaging piece 6a engages in an engaging hole 1a formed in the device body 1 side so as to maintain the door 6 in a closed state. The handle 5 is rotatably provided at the outer surface side of the door 6, and the engaged state can be released by gripping and pulling the handle 5. The lock pin 6b is a cylindrical shape with a circumferential groove formed in the outer circumferential surface, and a hook (not illustrated) having a roughly C-shape at the device body 1 side engages and disengages with the circumferential groove thereof. The lock pin 6b is capable of moving to an unlock position at which the hook engages onto the circumferential groove thereof, and a lock position at which the lock pin 6b is further penetrated into the device body 1 in an engaged state. Each of the abovementioned positions of the lock pin 6b and a middle position therebetween are detected by a sensor (not illustrated). Furthermore, a sensor (not illustrated) also determines whether or not the hook has rotated to the engaging position for engaging in the circumferential groove of the lock pin 6b. Note that a water level gage 11 (FIG. 1) is provided at the top left portion of the outer surface of the door 6 to display the water level inside the can body 2.

Figure 8:
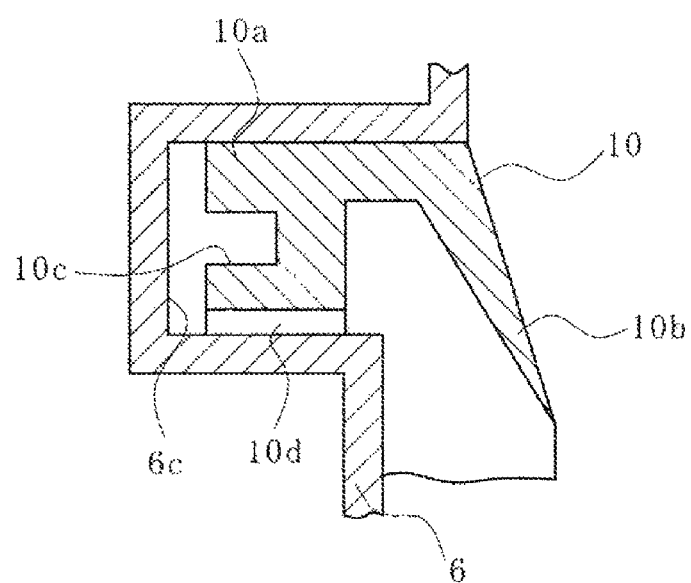
FIG. 8 is a schematic explanatory diagram of a packing shown in FIG. 2 and a mounting portion thereof.

A packing 10 is provided at a center part of the inner surface of the door 6 to increase the sealing performance when the door 6 is closed. In other words, an annular groove 6c is formed in the inner surface of the door 6. The packing 10 is made from a flexible material having excellent heat resistance such as silicone rubber, and is formed into a ring shape that can be press fitted into the annular groove 6c. More specifically, as shown in FIG. 8, the packing 10 is configured from an annular press fit part 10a that is press fit into the annular groove 6c, and an annular elastic tongue piece 10b projecting at an incline from an outer circumferential part at one end face of the annular press fit part 10a towards the inside. An annularly linking relief groove 10c is formed at a center position of the other end face of the annular press fit part 10a. Notches 10d communicating both end faces are formed at four equally spaced positions in the inner circumferential surface of the packing 10. Through the notches 10d, deformation of the annular press fit part 10a when mounting the packing 10 to the annular groove 6c of the door 6 is facilitated. Moreover, in the mounted state, a sealed space is not formed inside the annular groove 6c, and therefore the packing 10 can be reliably press fit as far as the prescribed position. Note that the packing 10 may also be provided on the device body side (around the opening part of the can body) rather than at the door 6. Furthermore, through-holes may also be formed in the packing 10 rather than notches. In short, when the packing 10 is press fitted into the annular groove 6c, a sealed space does not have to be formed by the annular groove 6c and the packing 10.

Figure 3:
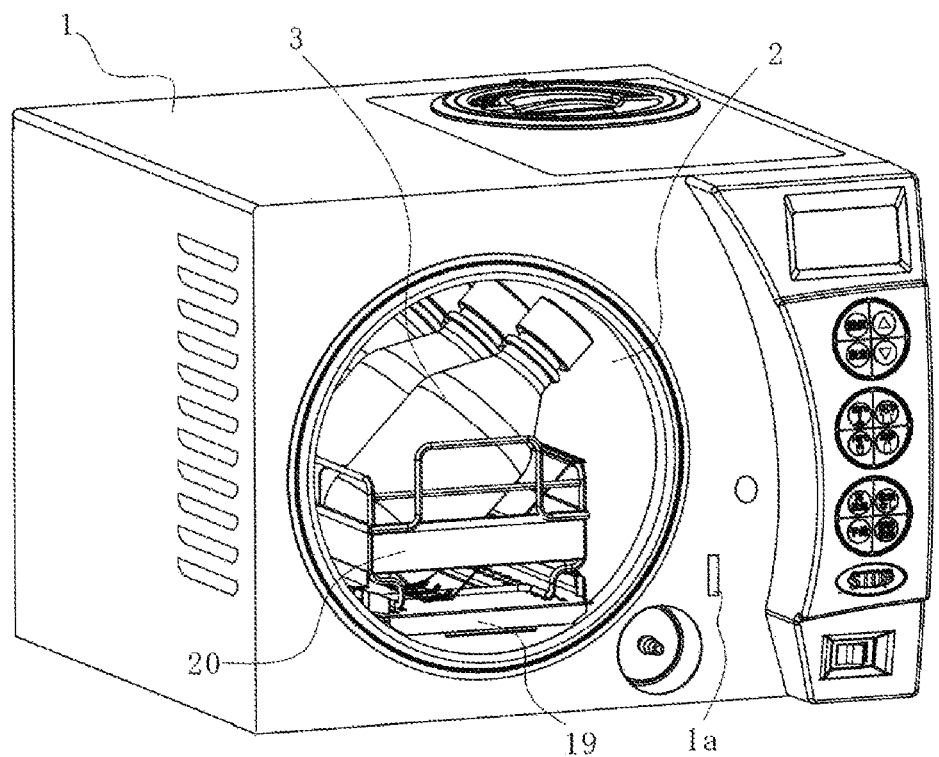
FIG. 3 is a perspective view showing a state with the door removed from the sterilizer shown in FIG. 1.
Figure 4:
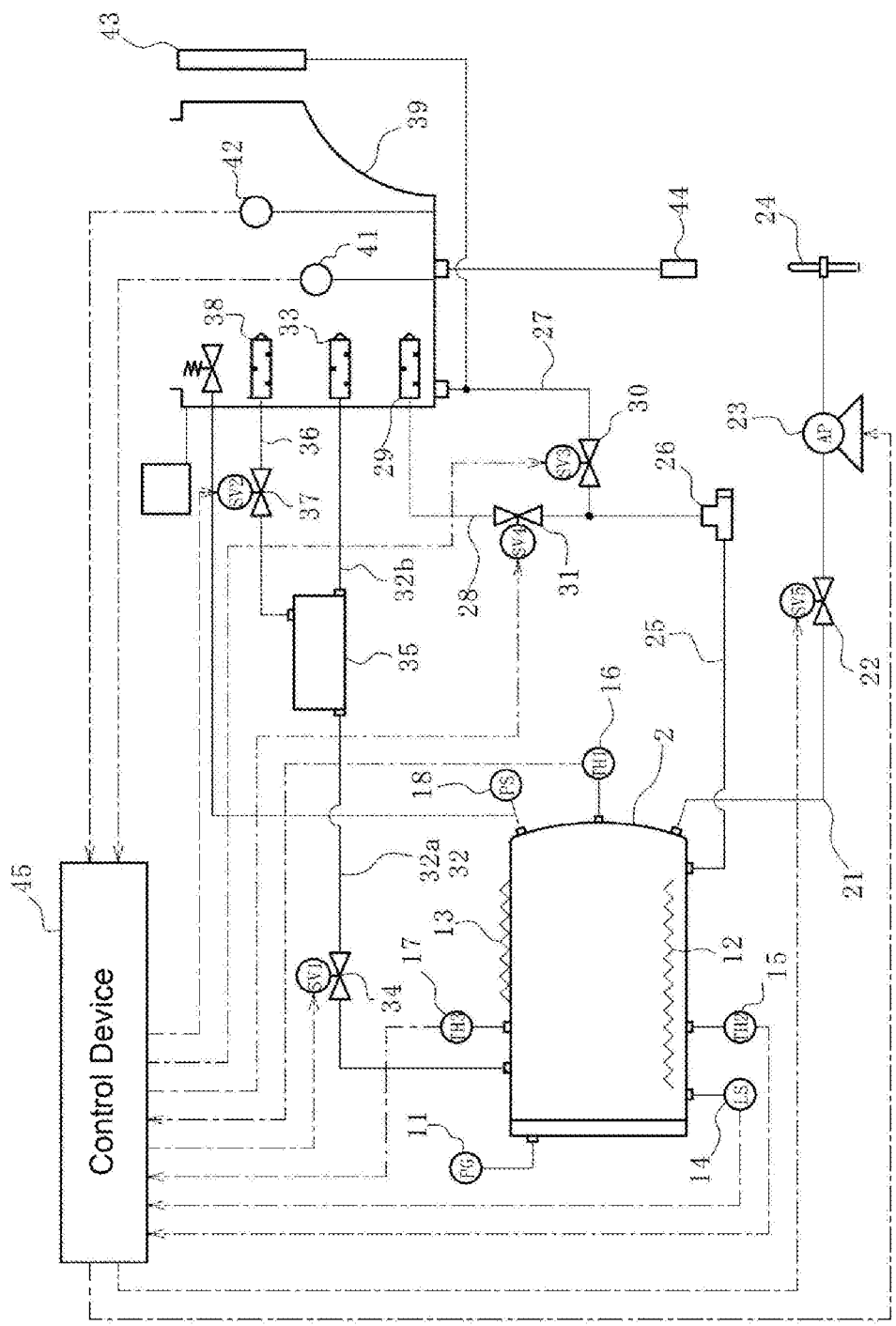
FIG. 4 is a piping system diagram of the sterilizer shown in FIG. 1.

As shown in FIG. 3, the can body 2 is a tubular shaped body formed from a conductive material such as stainless steel and having an opening at one end side, is arranged sideways such that the axial center thereof corresponds to the horizontal direction, and is grounded to thereby configure a negative electrode. As shown in FIG. 4, the can body 2 is provided with a sterilization heater 12, a drying heater 13, a water level electrode 14, an overheating detection thermistor 15, a first temperature regulation thermistor 16, a second temperature regulation thermistor 17, a pressure switch 18, and the like.

The sterilization heater 12 is provided at the base side of the can body 2, which is arranged sideways. As shown in FIG. 3, the top side of the sterilization heater 12 is covered by a support stage 19. An accommodation basket 20 for housing the object to be sterilized 3 (a drug bottle for example) is retrievably arranged on the support stage 19.

The drying heater 13 is arranged at an upper portion outside of the can body 2. The heater wires configuring the drying heater 13 are arranged in a zigzag shape so as to cover the top surface of the can body 2, and dry the inside of the can body 2.

The water level electrode 14 is provided so as to project upward from the bottom surface of the can body 2. Approximately ⅔ range of the water level electrode 14 from the bottom surface of the can body 2 is covered with an insulating material. Furthermore, conduction occurs when the water level inside the can body 2 rises and exceeds the insulated portion of the water level electrode 14, and therefore the supply of water to a prescribed water level can be detected based on the electrical signal thereof.

The overheating detection thermistor 15 is arranged at the bottom surface of the can body 2, and detects the temperature of the sterilization heater 12. The temperature detected by the overheating detection thermistor 15 is input into a below-described control device 45. The control device 45 controls the passage of electric current to the sterilization heater 12 based on the detected temperature input from the overheating detection thermistor 15, and forcibly discontinues the passage of electric current to the sterilization heater 12 when a preset abnormal temperature is exceeded.

The first temperature regulation thermistor 16 detects the temperature inside the can body 2, and outputs the detected temperature to the below-described control device 45. The control device 45 controls the passage of electric current to the sterilization heater 12 based on this detected temperature.

The second temperature regulation thermistor 17 is arranged at the top part of the can body 2, detects the temperature of the drying heater 13, and outputs the temperature thereof to the below-described control device 45. The control device 45 then controls the passage of electric current to the drying heater 13 based on this detected temperature.

The pressure switch 18 constantly detects the pressure inside the can body 2, and maintains the door 6 in a locked state when the detected pressure value exceeds the atmospheric pressure. Through this, it is possible to prevent the door 6 from being opened when the inside of the can body 2 is in a high pressure state.

A communicating pipe 21 is connected at the lower back surface of the can body 2. An air solenoid valve 22, an air pump 23, and an air filter 24 are provided in order from the can body 2 side partway along the communicating pipe 21. The air solenoid valve 22 is closed other than in the below-described standby state, and during drying treatment and air supply treatment.

A first piping 25 is connected to the bottom part of the can body 2. A strainer 26 is provided at the first piping 25. The first piping 25 branches into a water supply pipe 27 and a drainage pipe 28 at the side opposite the can body 2 with respect to the strainer 26. The water supply pipe 27 is connected to the bottom part of a water storage tank 39. The drainage pipe 28 pierces a lower side surface of the water storage tank 39 and extends internally, and a silencer 29 is attached at the tip end portion thereof. Moreover, a water supply solenoid valve 30 is provided partway along the water supply pipe 27, and a water discharge solenoid valve 31 is provided partway along the drainage pipe 28.

One end part of a second piping 32 is connected to the top part of the can body 2. The other end side of the second piping 32 pierces the below-described water storage tank 39, and a silencer 33 is attached to the tip end portion thereof. A steam discharge solenoid valve 34 and a discharged steam tank 35 are provided in order from the can body side partway along the second piping 32. As described below, the steam discharge solenoid valve 34 is controlled so as to open or close based on a control signal from the control device 45. The discharged steam tank 35 has a channel cross-sectional area that is sufficiently larger compared to that of the second piping 32 (upstream side piping), and here, the cross-sectional area is approximately ten times larger. Through this, steam discharged from the can body 2 and flowing through the upstream side piping and into the discharged steam tank 35 is reduced in pressure, and therefore the flow rate thereof is decreased, and the steam that is discharged (discharged steam) can be sufficiently cooled.

The second piping 32 has a channel cross-sectional area that differs between the upstream side piping 32a from the can body 2 to the discharged steam tank 35, and the downstream side piping 32b from the discharged steam tank 35 to the water storage tank 39, and the channel cross-sectional area of the upstream side piping 32a is approximately double that of the channel cross-sectional area of the downstream side piping 32b.

Moreover, the discharged steam tank 35 and the water storage tank 39 are also connected by a third piping 36 as well as the downstream side piping 32b. The third piping 36 has the same channel cross-sectional area as the upstream side piping 32a, and an exhaust gas solenoid valve 37 is provided in the middle thereof. A silencer 38 is attached to a tip end portion of the third piping 36 that penetrates into the water storage tank 39.

Note that sound muffling effects of the silencer 29 and the silencer 38 do not need to be much larger than that of the silencer 33. This is because only water discharged from the can body 2 passes through the silencer 29, and only steam of which the pressure has been reduced by first being discharged via the second piping 32 passes through the silencer 38.

The water storage tank 39 is housed inside the device body 1 at the right upper side of the can body 2 when viewed from the front. Water can be poured into the water storage tank 39 by opening a lid body 40 (see FIG. 1) provided at a top surface. A first water level sensor 41, a second water level sensor 42, and a water level gage 11 are provided at the water storage tank 39. The first water level sensor 41 detects a lower limit value of the water level of the water storage tank 39, and the second water level sensor 42 detects an upper limit value thereof. The detected water level is output to the below-described control device 45. A water level gage 43 makes it possible to view the water level inside the water storage tank 39 from outside the device body 1. A water discharge port 44 that is closed by a removable cap is formed in the bottom part of the water storage tank 39. Note that as described above, the water storage tank 39 and the can body 2 are connected by the first piping 25, the second piping 32 and the third piping 36.

As described below, the control device 45 receives input signals from the various sensors 14 to 17, 41, 42 and the like, and implements drive control of the various solenoid valves 22, 30, 31, 34, and 37, the air pump 23, and the like.

Next, operation of the sterilizer having the abovementioned configuration is described. In the sterilizer, a preparation treatment, a heating treatment, a sterilization treatment, a waste steam treatment, and a drying treatment are executed in order from a standby state. Each treatment is described in detail below based on the timing charts of FIG. 5 and FIG. 6.

(1) Preparation Treatment: In the preparation treatment, the object to be sterilized 3 is housed inside the can body 2, and the door 6 is closed, and in that state, a door motor is driven to create a locked state of the door 6. Furthermore, when the water discharge solenoid valve 31 is opened and the air pump 23 is driven, the water discharge process is executed for a prescribed amount of time (30 seconds in this example).

Next, the passage of electric current to the sterilization heater 12 and the drying heater 13 is started. PWM (Pulse Width Modulation) control with the rate of electric current passed to the sterilization heater 12 being 20% is performed until the temperature detected by the overheating detection thermistor 15 reaches 70° C. Moreover, the rate of electric current passed to the drying heater 13 is set to 100%, and control is implemented until the temperature detected by the second temperature regulation thermistor 17 reaches 70° C.

Next, if the temperature detected by each thermistor has reached 70° C. (preheat temperature), the passage of electric current to each heater 12, 13 is stopped, and the water supply solenoid valve 30 is opened to thereby initiate the supply of water to the inside of the can body 2 (water supply processing). The supply of water into the can body 2 is performed until the water level electrode 14 detects that the predetermined water level has been reached. Note that in the preparation process, both the steam discharge solenoid valve 34 and the exhaust gas solenoid valve 37 are left in the opened state.

(2) Heating Treatment: In the heating treatment, electric current is passed to the sterilization heater 12 with an electric current passage rate of 100% to heat the supplied water. Through this, steam is generated, and air in the can body 2 is discharged via the second piping 32. Furthermore, if the temperature detected by the first temperature regulation thermistor 16 reaches 95° C., the passage of electric current to the sterilization heater 12 is continued until a prescribed amount of time (3 minutes in this case) has passed.

Next, a determination is made as to whether or not a condition in which the temperature detected by the first temperature regulation thermistor 16 has exceeded 102° C. is satisfied, or whether or not a condition in which the difference between the temperature detected by the overheating detection thermistor 15 and the temperature detected by the first temperature regulation thermistor 16 has become 1° C. or less is satisfied. If either of the conditions is satisfied, a determination is made that all of the air in the can body 2 has been discharged and the can body 2 has been filled with steam, and the steam discharge solenoid valve 34 and the exhaust gas solenoid valve 37 are closed. However, if neither of the conditions is satisfied, heating by the sterilization heater 12 is extended for 7 minutes, and the opened states of the steam discharge solenoid valve 34 and the exhaust gas solenoid valve 37 are maintained until the abovementioned conditions are satisfied.

Next, a determination is made as to whether or not the temperature detected by the overheating detection thermistor 15 has reached the sterilization temperature (135° C. in this case). If the sterilization temperature has been reached, the sterilizer stands by until an equilibrium time (a fixed amount of time after the equilibrium state, or in other words, a state in which the sterilization temperature is maintained) has passed, and then transitions to the sterilization treatment.

(3) Sterilization Treatment: In the sterilization treatment, the passage of electric current to the sterilization heater 12 is controlled based on the temperature detected by the overheating detection thermistor 15 such that the sterilization temperature is maintained. Through this, the object to be sterilized 3 housed inside the can body 2 is sterilized by high temperature steam. Furthermore, once the sterilization time has passed, the sterilizer transitions to the steam and water discharge treatment.

(4) Steam and Water Discharge Treatment: The steam and water discharge treatment includes a steam discharge process, a first water discharge process, a second water discharge process, and a gas discharge process.

(4-1) Steam Discharge Process: In the steam discharge process, first, the steam discharge solenoid valve 34 (SV1) is opened. Through this, steam inside the can body 2 flows through the upstream side piping 32a of the second piping 32, through the discharged steam tank 35, through the downstream side piping 32b, and then is discharged to the water storage tank 39. The discharged steam tank 35 has a channel cross-sectional area that is sufficiently larger than that of the upstream side piping of the second piping 32. Therefore, the pressure of the steam from the can body 2 is reduced when the steam thereof flows from the upstream side piping and into the discharged steam tank 35. The steam is also cooled at the discharged steam tank 35, thereby decreasing in volume. As a result, the flow rate of the steam is slowed. Furthermore, the noise that is generated when the steam flows into the discharged steam tank 35 is mutually cancelled by the direct sound directly reaching the downstream side piping 32*b* and the reflected sound reflected by the inner wall of the discharged steam tank 35. Moreover, the channel cross-sectional area of the downstream side piping 32*b* is sufficiently smaller compared to that of the discharged steam tank 35. Therefore, when steam that has flowed into the discharged steam tank 35 flows out to the downstream side piping 32*b*, it is subjected to a large flow resistance, and the flow rate is further suppressed. Next, when time has passed from the startup of the steam discharge process, the steam that was in the can body 2 travels to the inside of the discharged steam tank 35, and the steam pressure inside the can body 2 decreases due to the inside of the discharged steam tank 35 being filled with steam, and the flow rate itself of the discharging steam decreases. Accordingly, the flow rate of the steam can be suppressed not only in the initial stage of the steam discharge process, but also thereafter as well. In this manner, when steam flows from the upstream side piping and into the discharged steam tank 35, noise is generated, but transmission of this noise to the outside is sufficiently suppressed. Furthermore, since the silencer 33 is provided at the tip end portion of the downstream side piping 32*b*, almost no noise is transmitted to the outside. After a prescribed amount of time has passed since initiating the steam discharge process (80 seconds in this case), the sterilizer transitions to the water discharge process.

(4-2) First Water Discharge Process: In the first water discharge process, the water discharge solenoid valve 31 (SV4) is opened following the steam discharge solenoid valve 34 (SV1). At this point in time, while steam is discharged via the second piping 32, the steam pressure inside the can body 2 is still maintained at a high state. Accordingly, water remaining in the can body 2 can be smoothly discharged to the water storage tank 39 via the first piping 25 by the steam pressure. In this manner, high pressure steam is first discharged in the steam discharge process, and then water is discharged in the first water discharge process. Accordingly, it is possible to suppress condensation of steam and adhesion thereof on the object to be sterilized 3 can be suppressed which would occur by first discharging water and reducing the pressure inside the can body 2.

(4-3) Second Water Discharge Process: In the second water discharge process, by allowing a prescribed amount of time (10 seconds in this case) to pass from the time that the water discharge solenoid valve 31 (SV4) was opened, the steam discharge solenoid valve 34 (SV1) is temporarily closed. Through this, it is possible to prevent defective discharging of the residual water which would occur by excessive dropping of the steam pressure inside the can body 2. Note that the silencer 29 is provided at the tip end portion of the drainage pipe 28. Accordingly, even when residual water is discharged from the can body 2, noise is not transmitted to the surrounding area.

(4-4) Gas Discharge Process: In the gas discharge process, when a prescribed amount of time (10 seconds in this case) has passed since the second water discharge process was initiated, a determination is made that all of the residual water inside the can body 2 has been discharged, and then the steam discharge solenoid valve 34 (SV1) is opened once again, and the water discharge solenoid valve 31 (SV4) is closed. At this time, the exhaust gas solenoid valve 37 (SV2) is also opened. Through this, steam inside the discharged steam tank 35 passes not only through the second piping 32 but also through the third piping 36, and is discharged to the water storage tank 39.

In this manner, steam is discharged from the can body 2 using not only the second piping 32, but also the third piping 36, and therefore this processing time can be further shortened. Moreover, at this time, the steam pressure inside the can body 2 is sufficiently reduced. Accordingly, the noise that is generated when the steam is discharged through the third piping 36 is not very large. Therefore, the noise is sufficiently reduced by the silencer 38 provided at the tip end of the third piping 36.

Next, if a prescribed amount of time (80 second in this case) has passed since steam discharge was initiated using the third piping 36 as well, driving of the air pump 23 is started, and the water discharge solenoid valve 31 (SV4) is temporarily opened. Here, the water discharge solenoid valve 31 (SV4) is temporarily opened in order to use the internal pressure to discharge the water remaining in the can body 2. Once a prescribed amount of time (30 seconds in this case) has passed since the driving of the air pump 23 was started, the gas discharge process is ended, and the sterilizer transitions to the drying treatment.

(5) Drying Treatment: In the drying treatment, driving of the air pump 23 is continued while controlling the passage of electric current to the sterilization heater 12 and the drying heater 13 until a prescribed drying time has passed after the completion of the gas discharge process. The drying time is automatically set depending on the difference in the types of objects to be sterilized 3, the difference in the drying mode (here, re-drying, no drying, scheduled, drying with door opened), and the like, which are set initially with the operation buttons 8.

Once the drying treatment has been completed, the passage of electric current to both heaters 12, 13 is stopped. Furthermore, by operating the stop button (of the operation buttons 8, the button positioned at the bottommost position), the door motor is driven to put the door in the unlocked state, and therefore the door 6 can be opened.

In this manner, according to the present embodiment, when steam is discharged from inside the can body 2, the steam is flowed through the second piping 32. Therefore, the speed can be reduced at the discharged steam tank 35 provided partway along the second piping 32, and then further reduced by the downstream side piping 32 having a large flow resistance. Accordingly, the noise that is generated can be suppressed.

As merely a reference, a sterilizer according to the present embodiment was used, the noise (units of dB) generated with each treatment was measured, and the results thereof are shown below. The measurements were performed 1 m in front of the sterilizer, and at a position of 1.2 m above the center position in the height direction of the device body. This measurement method complies with that of JIS Z 8737. Moreover, as the operation mode of the sterilizer, three types of sterilization were performed including 135° C. sterilization, 121° C. sterilization, and 115° C. sterilization. In the 135° C. sterilization, the sterilization time was 3 minutes, and the drying time was 30 minutes. In the 121° C. sterilization, the sterilization time was 20 minutes, and the drying time was 30 minutes. In the 115° C. sterilization, the sterilization time was 30 minutes, and the drying time was 30 minutes.

TABLE 1

| | Water Supply Treatment | Heating Treatment | Sterilization Treatment | Steam Discharge Treatment | Water Discharge Treatment | Drying Treatment |
|---|---|---|---|---|---|---|
| 135° C. | 37.2 | 42.1 | 36.8 | 49.0 | 47.9 | 45.9 |
| 121° C. | 37.1 | 42.5 | 36.1 | 42.8 | 46.8 | 45.2 |
| 115° C. | 36.8 | 41.8 | 35.8 | 42.4 | 48.3 | 45.8 |

As is clear from the measurement results, in each of the modes and each of the treatments, a noise level of 50 dB or less, which is required in the usage environment, was achieved. Note that when a configuration not provided with the discharged steam tank 35 was used and the same testing was performed, a noise level of 65 dB was measured in the steam discharge process, and a noise level of 60 dB was measured in the water discharge process.

Moreover, when the water is discharged from inside the can body 2, the water discharge solenoid valve 31 (SV4) is opened before lowering of the steam pressure inside the can body 2 is completed, which makes it possible to reduce the time for discharging water. Moreover, if the steam pressure inside the can body 2 is lowered, the steam discharge solenoid valve 34 (SV1) is closed, which makes it possible to prevent a reduction of the water discharge efficiency. In addition, not only the steam discharge solenoid valve 34 (SV1), but also the exhaust gas solenoid valve 37 (SV2) are opened after the water has been discharged, which makes it possible to exhaust gas through the second piping 32 and the third piping 36. Accordingly, it is possible to further reduce the time required for discharging steam.

Moreover, in the abovementioned embodiment, if the packing 10 deteriorates through long-term use, it can be replaced to ensure that the door is reliably locked, and the following type of positioning adjustment treatment may be implemented.

Figure 9:
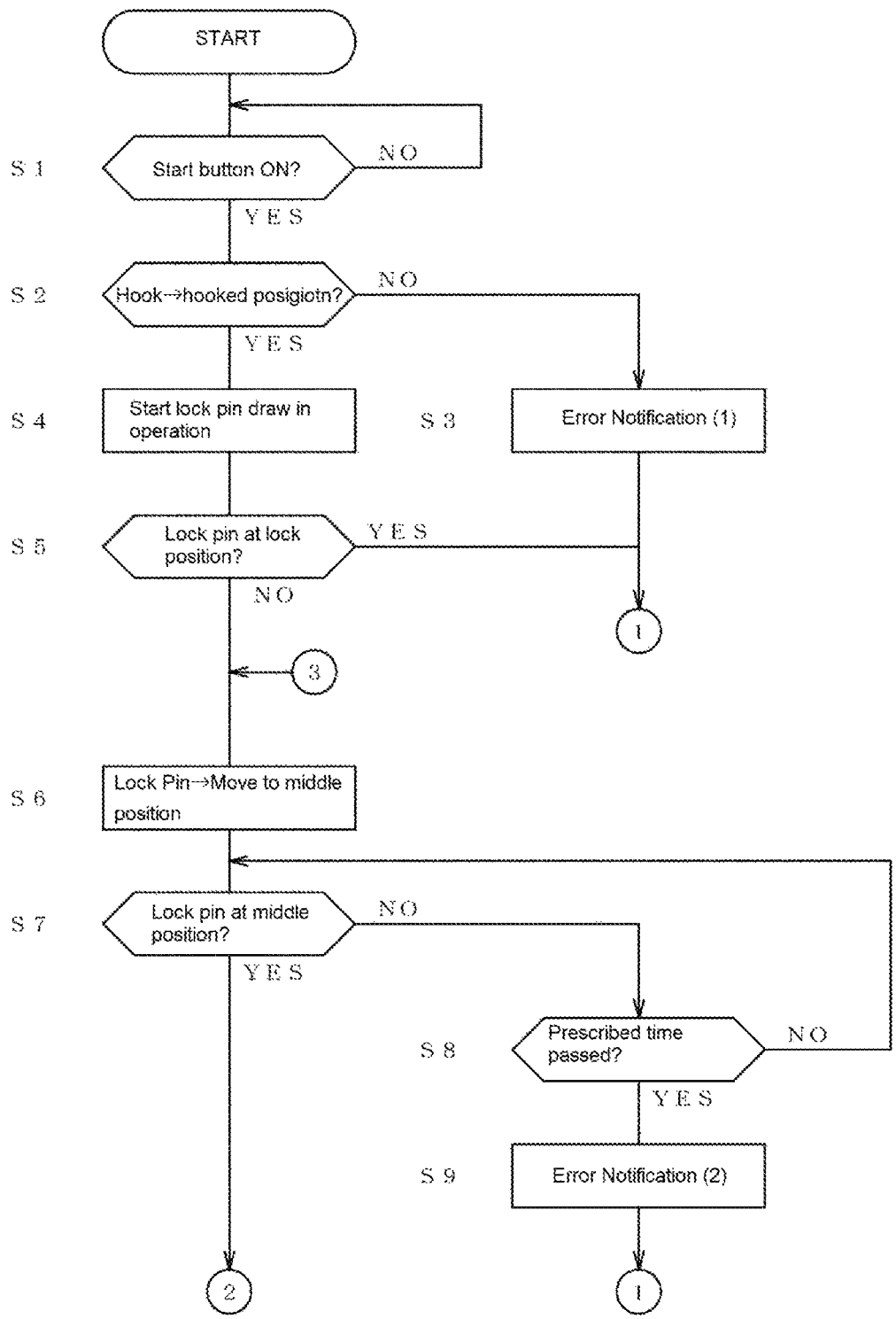
FIG. 9 is a flow chart showing a door locking operation after the packing shown in FIG. 2 is replaced.
Figure 10:
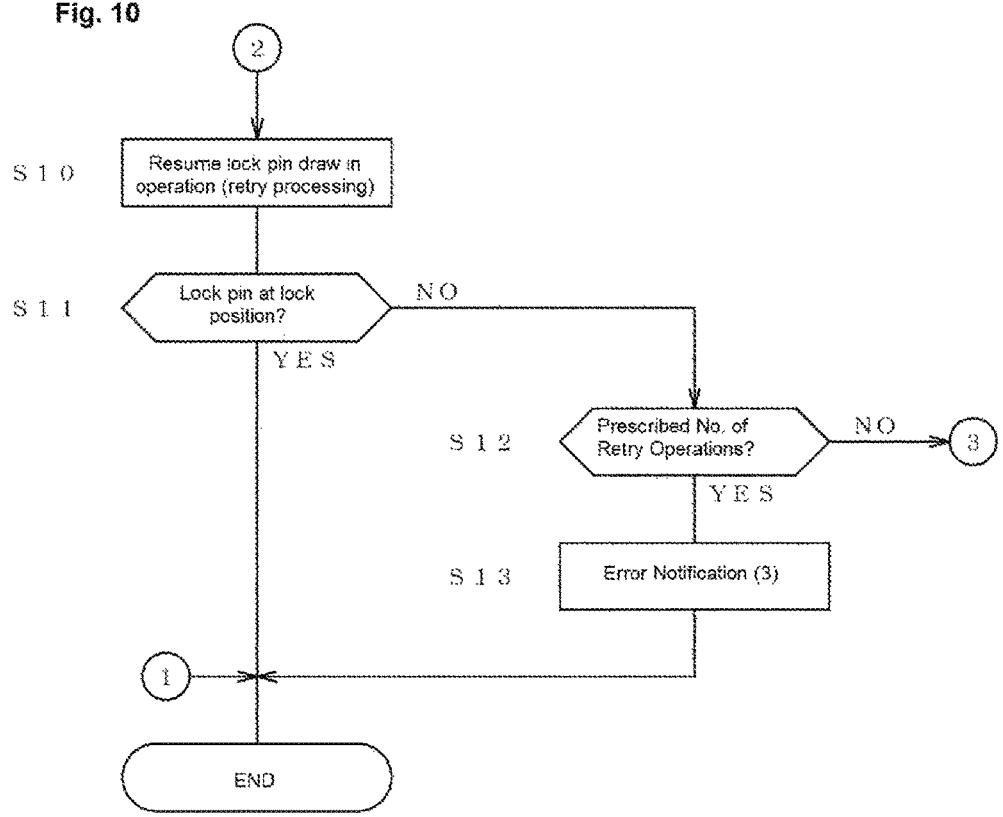
FIG. 10 is a flow chart showing a door locking operation after the packing shown in FIG. 2 is replaced.

Namely, as shown by the flow charts of FIG. 9 and FIG. 10, when the start button is operated (step S1), a determination is made regarding whether or not the door 6 is closed (step S2). This determination is made based on whether or not the engaging piece 6a on the door 6 side has been detected by a sensor (not illustrated) provided on the device body 1 side. If the door 6 is not closed, an error is notified (step S3).

If the door 6 is closed, the hook, which is a draw in means, is engaged onto the circumferential groove of the lock pin 6b and moved to thereby initiate a draw in operation to draw in the lock pin 6b from the unlock position to the lock position (step S4). If the lock pin 6b cannot be drawn to the lock position within a prescribed amount of time (30 seconds in this case) (step S5), this time the lock pin 6b is moved to a center position (step S6). If a prescribed amount of time (20 seconds in this case) passes without the lock pin 6b moving to the center position (step S8: YES), an error is notified (step S9). If the lock pin 6b reaches the center position (step S7: YES), the lock pin 6b is once again drawn to the lock position (step S10).

If the lock pin 6b reaches the lock position (step S11: YES), the processing is completed, but if the lock pin 6b does not reach the lock position (step S11: NO), a determination is made that the packing 10 is not mounted in its normal position, and is projecting from the inner surface of the door 6. Furthermore, until a retry operation has been implemented for a prescribed number of time (two times here) (step S12: NO), the processing returns to step S6, and the retry processing is performed to once again move the lock pin 6b to the center position, and resume the draw in operation. If the lock pin 6b cannot be drawn in to the lock position even after the retry operation has been completed for the prescribed number of times (step S12: YES), an error is notified (step S13) to prompt the user to confirm the mounting state of the packing 10.

In this manner, when the door 6 is closed after the packing 10 has been replaced, even if the packing 10 is not mounted in the normal position, the mounting position thereof can be automatically corrected by executing retry processing. In particular, by forming notches 10d in the inner circumferential surface of the packing 10, it becomes possible to prevent a sealed space from being formed in the annular groove 6c. Accordingly, with retry processing, the mounting position of the packing 10 can be easily corrected to the normal position.

Note that if notches 10d are not formed in the packing 10, even if the packing 10 is corrected to the normal position through the retry processing, a problem that the packing 10 jumps outward due to compressed air in the sealed space may occur.

The position adjustment treatments shown in the flow charts of FIG. 9 and FIG. 10 may be performed until the door 6 becomes in a locked state after a start button operation, which is the preparation process of FIG. 5, has been performed. Through this, the mounting position of the packing 10 can be ensured to be the normal position before the sterilization treatment is started.

Moreover, It is preferred that a "packing check mode" for performing the position adjustment treatment is provided, and appropriately executed by an operation on the display operation panel 4. According to the packing check mode, even if the user does not take time to correctly mount the packing 10 in the normal position, the user approximately mounts the packing 10 in the normal position, and then need only execute the "packing check mode". Therefore, the complexity of the packing 10 replacement operation can be significantly reduced.

Note that the present invention is not limited to the configuration described in the present embodiment, and various modifications can be made.

For example, in the abovementioned embodiment, the channel cross-sectional area of the upstream side piping 32a of the second piping 32 is approximately double the channel cross-sectional area of the downstream side piping 32b, but the channel cross-sectional areas are not limited thereto, and can be formed at various percentages. In other words, by making the channel cross-sectional area of the downstream side piping 32b to be smaller than that of the upstream side piping 32a, the flow rate can be further reduced, and the generation of noise can be suppressed. However, if the channel cross-sectional area of the downstream side piping 32b is too small, the discharging of steam from the can body 2 cannot be performed smoothly, and therefore the channel cross-sectional area must be set to the minimum limit necessary according to the amount of steam generated in the can body 2.

Moreover, in the abovementioned embodiment, the channel cross-sectional areas of the third piping 36 and the upstream side piping 32a of the second piping 32 are the same, but the cross-sectional area of the third piping 36 is preferably larger. Such a configuration makes it possible to further reduce the time required to discharge steam.

Furthermore, in the abovementioned embodiment, a communicating pipe 21 having the same inner diameter was used, but the inner diameter from the can body 2 to the air solenoid valve 22 (SV5) is preferably smaller than the inner diameter from the air solenoid valve 22 (SV5) to the air pump 23. Through this, vibration waves due to the flow of air discharged from the can body 2 can be suppressed. Moreover, compressed air in the air pump 23 functions as a damper, and therefore suppresses noise generated when the air pump 23 is driven from being transmitted to the outside.

Moreover, in the abovementioned embodiment, the upstream side piping 32a and the downstream side piping 32b of the second piping 32 are arranged on the same axial center, but the upstream side piping 32a and the downstream side piping 32b are preferably arranged such that the axial centers of both are shifted. Through this, the noise that is generated when steam is discharged from the upstream side piping 32a to the discharged steam tank 35 is not transmitted straight ahead in the flow direction of the steam, and is not directly transmitted to the outside through the downstream side piping 32b. In other words, the noise that is generated when the steam flows into the discharged steam tank 35 becomes difficult to be directly transmitted through the downstream side piping 32b, and is reflected inside the discharged steam tank 35 and mutually cancelled. Accordingly, the sterilizer can exhibit further excellent soundproofing performance.

Figure 12:
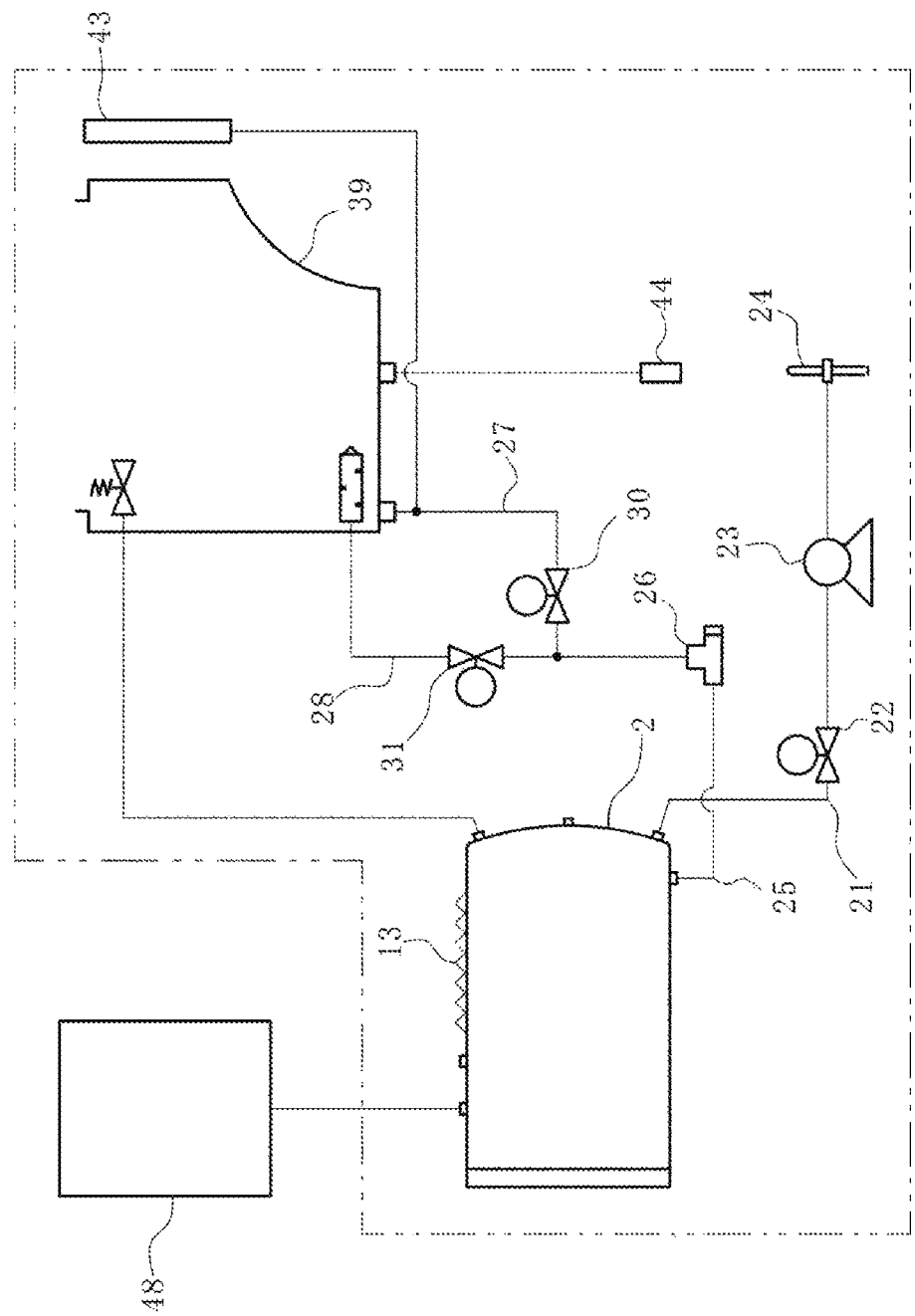
FIG. 12 is a rough sketch showing the piping system of a sterilizer according to another embodiment.

Furthermore, in the abovementioned embodiment, a configuration having the sterilization heater 12 inside the can body 2 was described, but the steam does not necessarily have to be generated inside the can body 2. As shown in FIG. 12, the sterilizer may be configured such that a steam generator 48 is provided separately from the can body 2, and steam generated by this steam generator 48 is supplied to the inside of the can body 2. Note that in FIG. 12, the configurations other than the steam discharging line are the same as those shown in FIG. 2, and those portions other than the main portions have been omitted.

Moreover, in the abovementioned embodiment, the discharged steam tank 35 was configured with a cylindrical container, but the configuration is not limited thereto, and the discharged steam tank 35 may have any configuration as long as it is capable of weakening the force of the steam discharged from the second piping 32. Of course, if the second piping 32 is configured so as to have a sufficient length, the same effect can be obtained, but such a configuration leads to an increase in the size of the sterilizer. In this regard, the discharged steam tank 35 is superior in terms of having a simple, inexpensive configuration and not leading to an increase in the size of the device.

Furthermore, the discharged steam tank 35 can also be merely configured with an expanded diameter part at which the channel cross-sectional area of the second piping 32 is enlarged in the middle thereof. For example, the expanded diameter part may be configured by enlarging the cross-sectional area of the second piping 32 along the flow direction, or by enlarging the cross-sectional area and then reducing it. Moreover, the cross-sectional shape thereof is not limited to a circular shape, and may be a quadrilateral shape or other various shapes. In addition, when the steam is not flowing, the inside of the discharged steam tank 35 may be freely designed to be an airtight state or a non-airtight state. If the discharged steam tank 35 is designed to be an airtight state, the entrance and exit of the discharged steam tank may be opened at the preferable timing for the discharging of steam.

Figure 11:
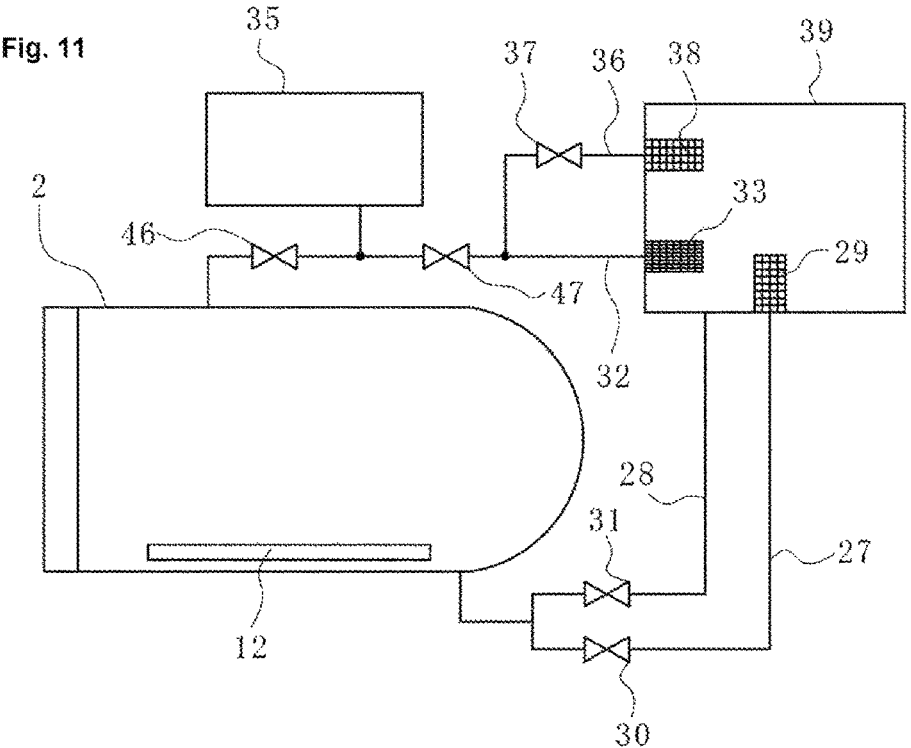
FIG. 11 is a rough sketch showing the piping system of a sterilizer according to another embodiment.

Moreover, in the abovementioned embodiment, steam discharged from the can body 2 is made to flow directly into the discharged steam tank 35 through the second piping 32, but the configuration shown in FIG. 11 can also be adopted.

Namely, the discharged steam tank 35 is provided partway along the third piping 36 branched from the second piping 32. A first solenoid valve 46 and a second solenoid valve 47 are respectively provided at the upstream side and the downstream side of the branching position. Note that while simplified in the drawing, the other configurations are the same as the abovementioned embodiment.

In the sterilizer of the abovementioned configuration, when steam is discharged from the can body 2, the first solenoid valve 46 is opened with the second solenoid valve 47 in a closed state, and discharged steam flows into the discharged steam tank 35. Since the second solenoid valve 47 is closed, the sound that is generated when steam flows from the can body 2 and into the discharged steam tank 35 does not leak to the outside. Furthermore, once the amount of time assumed to be needed for the steam to fill the inside of the discharged steam tank 35 has passed, the first solenoid valve 46 is closed, and the second solenoid valve 47 is opened. Through this, steam inside the discharged steam tank 35 of which the pressure has been sufficiently reduced compared to the steam inside the can body 2 can be discharged to the water storage tank 39. Accordingly, almost no noise is generated in this stage. Hereinafter, until the pressure inside the can body 2 has been sufficiently lowered, the steps of (1) closing the second solenoid valve 47 and opening the first solenoid valve 46, and (2) closing the first solenoid valve 46 and opening the second solenoid valve 47 are repeated. If the pressure inside the can body 2 has been sufficiently reduced, both the first solenoid valve 46 and the second solenoid valve 47 are opened.

Note that the timing at which the first solenoid valve 46 and the second solenoid valve 47 are opened and closed is managed by time, but the timing thereof can also be managed based on the detected pressure value obtained by detecting the pressure inside the discharged steam tank 35. Moreover, the opening and closing of the first solenoid valve 46 and the second solenoid valve 47 is repeated, but if a large capacity tank is used for the discharged steam tank 35, the number of repetitions can be reduced, and the need for repetition can even be eliminated.

Furthermore, in the abovementioned embodiment, the water storage tank 39 was given as an example of the discharged steam cooling unit, but the discharged steam cooling unit is not limited thereto, and may be configured such that steam is discharged outside the device body 1 through a cooling unit such as a radiator, or the steam is discharged outside the device body 1 through a housing unit other than the water storage tank 39. Moreover, the discharged steam cooling unit may be configured with a container provided outside the device body 1, a water discharge port or the like at a position where there is no direct human contact.

Moreover, in the abovementioned embodiment, the steam and water discharge treatment is executed as described above. However, depending on the housing state of the object to be sterilized (such as if a large quantity of objects to be sterilized made of metal are housed), the pressure of the can body cannot be sufficiently reduced in the above-described (4-1) steam discharge process. In this case, when the above-described (4-2) first water discharge process is implemented, water and air are discharged to the water storage tank 39 with strong force, which often causes noise. As a countermeasure thereto, the steam and water discharge treatment shown in FIG. 13 is preferably implemented as described below.

(Steam and Water Discharge Treatment) In the first step, the steam discharge solenoid valve 34 (SV1) is opened for a prescribed amount of time. The opening time of the steam discharge solenoid valve 34 varies depending on the sterilization temperature that was set. For example, if the sterilization temperature is 135° C., the opening time is 60 seconds. Moreover, if the sterilization temperature is 121° C., the opening time is 80 seconds, and if the temperature thereof is 115° C., the opening time is 40 seconds. The opening time is longer for a sterilization temperature of 121° C. than for a sterilization temperature of 135° C., which is because a second step, which will be described below, is omitted. For the same reason, the below-described second step is omitted for the case in which the sterilization temperature is 115° C. as well. Through this, the steam inside the can body 2 flows through the upstream side piping 32a of the second piping 32, passes through the discharged steam tank 35, passes through the downstream side piping 32b, and then is discharged to the water storage tank 39. During this time, similar to the abovementioned steam discharge process, the noise that is generated is suppressed, and almost no noise is leaked to the outside. In addition, unlike the steam and water discharge treatment, in the first step and the below-described second step, the passage of electric current to the sterilization heater 12 and the drying heater 13 is stopped. Through this, it is possible to prevent the inside pressure of the can body 2 from being maintained at a high pressure due to steam generated by heating water thereinside during the steam discharge process.

In the second step, the exhaust gas solenoid valve 37 (SV2) is opened for a prescribed amount of time (20 seconds in this case), and steam inside the can body 2 is discharged via the third piping 36 as well as the second piping 32. As described above, the steam pressure inside the can body 2 is sufficiently reduced by increasing the opening time of the steam discharge solenoid valve 34, and therefore even if the steam is discharged from the third piping 36 by opening the exhaust gas solenoid valve 37, the noise level does not increase to such an extent that may cause a problem. Here, the pressure inside the can body 2 in the case that the sterilization temperature is 121° C. is reduced compared to that in the case that the sterilization temperature is 135° C. Therefore, if the second step is executed, steam is discharged unnecessarily such that the pressure inside the can body 2 is reduced to a level that negatively affects the later water discharge process. For this reason, in the case that the sterilization temperature is 121° C., the second step is omitted. For the same reason, the second step is also omitted in the case that the sterilization temperature is 115° C. Note that the exhaust solenoid valve 37 is designed such that it is opened only for the predetermined amount of opening time, but the exhaust solenoid valve 37 may be designed to be opened when the steam pressure inside the can body 2 is detected by a sensor or the like separately provided and is at or below a set pressure.

In the third step, the exhaust gas solenoid valve 37 (SV2) is closed, and the water discharge solenoid valve 31 (SV4) is opened for a prescribed amount of time (30 seconds in this case). Through this, steam is discharged through the second piping 32, and water is discharged through the first piping 25 and the drainage pipe 28. During this time, an operation, in which the water discharge solenoid valve 31 (SV4) is opened for a prescribed amount of time (1 second in this case), and then closed for a prescribed amount of time (0.5 seconds in this case), is repeated. Here, when the water discharge solenoid valve 31 is opened for a prescribed amount of time or longer, air together with the water inside the can body 2 is pulled towards the first piping 25 side and reaches the water storage tank 39, and as a result, a "gurgling" noise is generated. For this reason, the water discharge solenoid valve 31 is opened and closed. By repeating the opening and closing operations of the water discharge solenoid valve 31, since only water is sent to the water storage tank 39, the generation of this type of noise can be prevented.

In the fourth step, the water discharge solenoid valve 31 (SV4) is closed, and the exhaust gas solenoid valve 37 (SV2) is opened for a prescribed amount of time (70 seconds in this case). Through this, steam is discharged from the second piping 32 and the third piping 36.

In the fifth step, the state of discharging steam from the second piping 32 and the third piping 36 is continued (for 30 seconds in this case), and at the same time, the air pump 23 is driven. Moreover, the water discharge solenoid valve 31 (SV4) is temporarily opened (for 10 seconds), and the pressure inside the can body 2 is raised to thereby discharge water from the first piping 25 and the drainage pipe 28.

In this manner, in the first step, the opening time for the steam discharge solenoid valve 34 is set to be long, and therefore the steam pressure inside the can body 2 can be reduced to such a level that noise generated by opening the exhaust gas solenoid valve 37 does not become a problem. Furthermore, in the third step, the opening and closing operations of the water discharge solenoid valve 31 are repeated, and therefore noise is not generated when water is discharged as well. Accordingly, the generation of noise can be suppressed as far as possible such that the sterilizer of the present invention is suited for use in locations that require quietness.

Note that if some sort of error is generated in the sterilization treatment or the like, the steam discharge solenoid valve 34 and the exhaust gas solenoid valve 37 are opened for a prescribed amount of time (210 seconds in this case) without performing such control that was implemented in the steam discharge process. Through this, the pressure inside the can body 2 can be rapidly reduced, and therefore the object to be sterilized can be quickly removed.

What is claimed is:
1. A sterilizer comprising:
a can body having a heater, and capable of housing an object to be sterilized; and
a steam discharge pipe connected to the can body and having an opening and closing valve for opening and closing a channel;
wherein the steam discharge pipe has an expanded diameter part at which an inner diameter dimension of the steam discharge pipe is enlarged;
wherein the steam discharge pipe includes an upstream side piping forming a path from the can body to a discharged steam tank provided partway along the steam discharge pipe and having a greater channel cross-sectional area than a channel cross-sectional area of the steam discharge pipe; and a downstream side piping connected to the discharged steam tank and a discharged steam cooling unit for cooling the steam discharged from the discharged steam tank before the steam reaches outside,
and wherein a channel cross-sectional area of the downstream side piping is smaller than a channel cross-sectional area of the upstream side piping.
2. The sterilizer according to claim 1, wherein a second steam discharge pipe connected to the discharged steam tank and the discharged steam cooling unit, and having an opening and closing valve for opening and closing a channel is connected.

3. The sterilizer according to claim 1, wherein a second steam discharge pipe connected to the discharged steam tank and the discharged steam cooling unit, and having an opening and closing valve for opening and closing a channel is connected, and the second steam discharge pipe has a larger channel cross-sectional area than that of the downstream side piping of the steam discharge pipe.

4. The sterilizer according to claim 1, wherein the discharged steam cooling unit is a water storage tank.

5. The sterilizer according to claim 4, further comprising a piping connected to the can body, and having an opening and closing valve for opening and closing a channel to enable discharging of water,
wherein the piping is branched into a water supply pipe capable of supplying the water from the water storage tank and a drainage pipe capable of discharging the water to the water storage tank.

6. The sterilizer according to claim 1, wherein axial center positions of the upstream side piping and the downstream side piping connected to the discharged steam tank are displaced.

7. A sterilizer comprising:
a can body capable of housing an object to be sterilized;
a steam generator for generating steam and supplying the steam to the can body; and
a steam discharge pipe connected to the can body and having an opening and closing valve for opening and closing a channel;
wherein the steam discharge pipe has an expanded diameter part at which an inner diameter dimension of the steam discharge pipe is enlarged;
wherein the steam discharge pipe includes an upstream side piping forming a path from the can body to a discharged steam tank provided partway along the steam discharge pipe and having a greater channel cross-sectional area than a channel cross-sectional area of the steam discharge pipe; and a downstream side piping connected to the discharged steam tank and a discharged steam cooling unit for cooling the steam discharged from the discharged steam tank before the steam reaches outside,
and wherein a channel cross-sectional area of the downstream side piping is smaller than a channel cross-sectional area of the upstream side piping.

8. The sterilizer according to claim 7, wherein a second steam discharge pipe connected to the discharged steam tank and the discharged steam cooling unit, and having an opening and closing valve for opening and closing a channel is connected.

9. The sterilizer according to claim 7, wherein a second steam discharge pipe connected to the discharged steam tank and the discharged steam cooling unit, and having an opening and closing valve for opening and closing a channel is connected, and the second steam discharge pipe has a larger channel cross-sectional area than that of the downstream side piping of the steam discharge pipe.

10. The sterilizer according to claim 7, wherein the discharged steam cooling unit is a water storage tank.

11. The sterilizer according to claim 10, further comprising a piping connected to the can body, and having an opening and closing valve for opening and closing a channel to enable discharging of water,
wherein the piping is branched into a water supply pipe capable of supplying the water from the water storage tank and a drainage pipe capable of discharging the water to the water storage tank.

12. The sterilizer according to claim 7, wherein axial center positions of the upstream side piping and the downstream side piping connected to the discharged steam tank are displaced.

* * * * *